United States Patent
Johnson et al.

(10) Patent No.: US 10,725,003 B2
(45) Date of Patent: Jul. 28, 2020

(54) AUTOMATIC BUMP AND CALIBRATION IN GAS DETECTORS VIA SHORT RANGE COMMUNICATION

(71) Applicant: Honeywell International Inc., Morris Plains, NJ (US)

(72) Inventors: Kirk William Johnson, Calgary (CA); Kelly Englot, Calgary (CA); Stephen Mroszczak, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 313 days.

(21) Appl. No.: 15/541,656

(22) PCT Filed: Jan. 12, 2016

(86) PCT No.: PCT/US2016/012942
§ 371 (c)(1),
(2) Date: Jul. 5, 2017

(87) PCT Pub. No.: WO2016/118355
PCT Pub. Date: Jul. 28, 2016

(65) Prior Publication Data
US 2018/0267003 A1     Sep. 20, 2018

Related U.S. Application Data

(60) Provisional application No. 62/105,158, filed on Jan. 19, 2015.

(51) Int. Cl.
*G01N 33/00* (2006.01)
*H04B 5/00* (2006.01)
(Continued)

(52) U.S. Cl.
CPC ......... *G01N 33/0006* (2013.01); *G08B 21/12* (2013.01); *G08B 25/08* (2013.01);
(Continued)

(58) Field of Classification Search
CPC ........... G01N 33/0006; G01N 33/0008; H04Q 2209/47
(Continued)

(56) References Cited

U.S. PATENT DOCUMENTS

| | | |
|---|---|---|
| 4,525,266 A | 6/1985 | Schmidt et al. |
| 5,068,798 A | 11/1991 | Heath et al. |

(Continued)

FOREIGN PATENT DOCUMENTS

| | | |
|---|---|---|
| AU | 2016213793 A1 | 3/2016 |
| AU | 2016213795 A1 | 3/2017 |

(Continued)

OTHER PUBLICATIONS

PCT Application No. PCT/US2016/012924, International Search Report, dated Apr. 5, 2016, 4 pages.
(Continued)

*Primary Examiner* — Robert R Raevis
(74) *Attorney, Agent, or Firm* — Alston & Bird LLP

(57) ABSTRACT

Embodiments relate generally to systems and methods for completing processes on a gas detector device using near-field communication between the gas detector device and an NFC tag. The NFC tag may communicate instructions or information to the gas detector device. The NFC tag may be located on or near a gas testing system, comprising gas deliver tube(s), gas tank(s), as well as other elements. In some embodiments, the gas detector device may comprise a single button to simplify interactions with the user.

20 Claims, 3 Drawing Sheets

(51) Int. Cl.
*H04Q 9/00* (2006.01)
*G08B 21/12* (2006.01)
*G08B 25/08* (2006.01)

(52) U.S. Cl.
CPC .............. *H04B 5/0056* (2013.01); *H04Q 9/00* (2013.01); *H04Q 2209/47* (2013.01)

(58) Field of Classification Search
USPC ...................... 73/1.06; 702/100, 104, 87, 88
See application file for complete search history.

(56) References Cited

U.S. PATENT DOCUMENTS

| | | | |
|---|---|---|---|
| 5,468,968 A | 11/1995 | Bailey et al. | |
| 6,720,866 B1 | 4/2004 | Sorrells et al. | |
| 6,809,646 B1 | 10/2004 | Lee | |
| 7,281,404 B2 * | 10/2007 | Peng | G01N 1/2226 73/1.03 |
| 7,397,370 B2 | 7/2008 | Bratkovski | |
| 7,782,224 B2 | 8/2010 | Marchetti | |
| 8,271,208 B1 | 9/2012 | Bolinger et al. | |
| 8,618,914 B2 | 12/2013 | Bachman et al. | |
| 8,624,725 B1 | 1/2014 | MacGregor | |
| 8,952,821 B2 * | 2/2015 | Erdtmann | G01N 21/53 250/574 |
| 9,705,570 B2 | 7/2017 | Mroszczak et al. | |
| 9,743,221 B2 | 8/2017 | Javer et al. | |
| 2001/0040512 A1 | 11/2001 | Hines et al. | |
| 2002/0190866 A1 | 12/2002 | Richardson | |
| 2003/0000281 A1 * | 1/2003 | Ketler | G01N 33/0006 73/1.06 |
| 2004/0055359 A1 * | 3/2004 | Ketler | G01N 33/0006 73/1.07 |
| 2005/0088299 A1 | 4/2005 | Bandy et al. | |
| 2005/0127297 A1 * | 6/2005 | Starta | G01N 21/3504 250/341.5 |
| 2006/0237648 A1 | 10/2006 | Bushberg | |
| 2007/0013516 A1 | 1/2007 | Freitag et al. | |
| 2007/0052540 A1 | 3/2007 | Hall et al. | |
| 2007/0241261 A1 | 10/2007 | Wendt | |
| 2008/0030324 A1 | 2/2008 | Bekritsky et al. | |
| 2008/0101400 A1 | 5/2008 | Auterinen | |
| 2008/0159547 A1 | 7/2008 | Schuler et al. | |
| 2008/0231836 A1 | 9/2008 | Curello et al. | |
| 2009/0058635 A1 | 3/2009 | LaLonde et al. | |
| 2009/0058648 A1 | 3/2009 | Tuttle | |
| 2009/0091465 A1 | 4/2009 | Buckingham et al. | |
| 2009/0184165 A1 | 7/2009 | Bertness et al. | |
| 2009/0231099 A1 | 9/2009 | Hyde et al. | |
| 2010/0212395 A1 * | 8/2010 | Willett | G01N 33/0073 73/1.06 |
| 2010/0241464 A1 | 9/2010 | Amigo et al. | |
| 2010/0326165 A1 * | 12/2010 | Rauworth | G01N 33/0006 73/1.06 |
| 2011/0037599 A1 | 2/2011 | Johnson, Jr. et al. | |
| 2011/0043373 A1 | 2/2011 | Best et al. | |
| 2011/0248857 A1 * | 10/2011 | Rutherford | G08B 21/16 340/632 |
| 2012/0007736 A1 * | 1/2012 | Worthington | G08B 17/117 340/539.22 |
| 2012/0063956 A1 | 3/2012 | Truex et al. | |
| 2012/0161967 A1 | 6/2012 | Stern | |
| 2013/0002405 A1 | 1/2013 | Pesonen et al. | |
| 2013/0244615 A1 | 9/2013 | Miller | |
| 2014/0028819 A1 | 1/2014 | Nakano | |
| 2014/0293306 A1 | 10/2014 | Tredoux et al. | |
| 2014/0336920 A1 | 11/2014 | Burrell et al. | |
| 2014/0349707 A1 | 11/2014 | Bang | |
| 2015/0102926 A1 | 4/2015 | Kamalakannan et al. | |
| 2015/0116093 A1 | 4/2015 | Swager et al. | |
| 2015/0269818 A1 | 9/2015 | Jain et al. | |
| 2015/0276540 A1 * | 10/2015 | Huseynov | G01M 3/007 73/1.06 |
| 2016/0209386 A1 * | 7/2016 | Belski | G01N 33/0063 |
| 2017/0047969 A1 | 2/2017 | Mroszczak et al. | |
| 2017/0048650 A1 | 2/2017 | Javer et al. | |

FOREIGN PATENT DOCUMENTS

| | | |
|---|---|---|
| CN | 106442883 A1 | 2/2017 |
| CN | 106469286 A | 3/2017 |
| CN | 107113480 A | 8/2017 |
| EP | 2887062 A2 | 6/2015 |
| EP | 3131008 A1 | 2/2017 |
| EP | 3131308 A1 | 2/2017 |
| EP | 3248384 A1 | 11/2017 |
| GB | 2345971 A | 7/2000 |
| JP | 2006003115 A | 1/2006 |
| WO | 9207261 A1 | 4/1992 |
| WO | 2012006090 A1 | 1/2012 |
| WO | 2013185821 A1 | 12/2013 |
| WO | 2016118355 A1 | 7/2016 |

OTHER PUBLICATIONS

PCT Application No. PCT/US2016/012924, Written Opinion of the International Searching Authority, dated Apr. 5, 2016, 5 pages.
PCT Application No. PCT/US2016/012942, International Preliminary Report on Patentability, dated Jul. 25, 2017, 6 pages.
Europe Patent Application No. 16701893.6, Communication pursuant to Rules 161(1) and 162 EPC, dated Aug. 25, 2017, 2 pages.
PCT Application No. PCT/US2016/012942, International Search Report, dated Apr. 5, 2016, 4 pages.
PCT Application No. PCT/US2016/012942, Written Opinion of the International Searching Authority, dated Apr. 5, 2016, 5 pages.
PCT Application No. PCT/US2016/026321, International Search Report, dated Jun. 2, 2016, 3 pages.
PCT Application No. PCT/US2016/026321, Written Opinion of the International Searching Authority, dated Jun. 2, 2016, 6 pages.
U.S. Appl. No. 16/091,902, filed Oct. 5, 2018, 21 pages.
U.S. Appl. No. 14/825,081, Office Action, dated Jun. 7, 2016, 20 pages.
U.S. Appl. No. 14/825,081, Final Office Action, dated Oct. 19, 2016, 18 pages.
U.S. Appl. No. 14/825,081, Advisory Action, dated Jan. 20, 2017, 4 pages.
U.S. Appl. No. 14/825,081, Notice of Allowance, dated Mar. 1, 2017, 7 pages.
U.S. Appl. No. 14/825,081, Supplemental Notice of Allowability, dated Jun. 8, 2017, 2 pages.
U.S. Appl. No. 14/825,097, Office Action, dated Jun. 2, 2016, 18 pages.
U.S. Appl. No. 14/825,097, Final Office Action, dated Sep. 14, 2016, 18 pages.
U.S. Appl. No. 14/825,097, Notice of Allowance, dated Dec. 2, 2016, 16 pages.
U.S. Appl. No. 14/825,097, Notice of Allowance, dated Apr. 26, 2017, 7 pages.
Europe Patent Application No. 16182897.5, Extended European Search Report, dated Nov. 21, 2016, 11 pages.
Whitson Gordon: "How to Automate Your Phone for Every Room in the House with NFC Tags", Lifehacker, Apr. 16, 2013, Retrieved from the Internet: http://lifehacker.com/how-to-automate-your-phone-for-every-room-in-the-house-473409962, retrieved on Jun. 23, 2015, 6 pages.
Europe Patent Application No. 16182884.3, Extended European Search Report, dated Dec. 15, 2016, 8 pages.
Office Action for related Chinese Application No. 201680006197.7 dated Apr. 7, 2020, 8 pages.

* cited by examiner

AUTOMATIC BUMP AND CALIBRATION IN GAS DETECTORS VIA SHORT RANGE COMMUNICATION

CROSS-REFERENCE TO RELATED APPLICATIONS

The present application claims priority to and is the National Stage of International Application No. PCT/US2016/012942 (entitled AUTOMATIC BUMP AND CALIBRATION IN GAS DETECTORS VIA SHORT RANGE WIRELESS COMMUNICATION filed Jan. 12, 2016), which claims priority to U.S. Provisional Patent Application Ser. No. 62/105,158 (entitled AUTOMATIC BUMP AND CALIBRATION IN GAS DETECTORS VIA SHORT RANGE WIRELESS COMMUNICATION filed Jan. 19, 2015), both of which are incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be carried by workers in environments where there is potential for harmful gases. The gas detectors may be periodically tested and/or calibrated to ensure that the detector is working properly. This may be done using a gas testing system operable to supply a sample gas to the detector and analyze the response of the gas detector. In some workplaces, the testing may occur while a user is wearing other protective gear, such as gloves, suits, helmets, respiratory equipment, etc.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
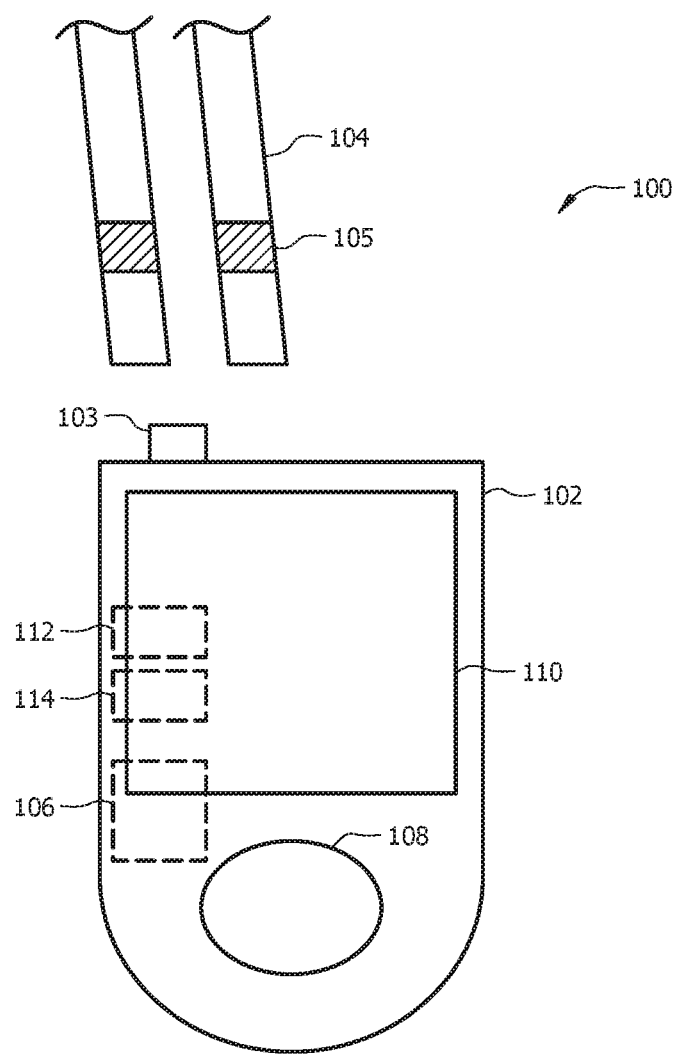
FIG. 1A illustrates a gas detector and gas delivery tubes according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

There is a strong desire for compliance based portable gas detectors to be as user friendly as possible. One of the ways this can be accomplished is by limiting the device to a single button, reducing the interaction between the user and device. One of the issues with this arises if multiple types of user/device interactions are required, and it becomes difficult to come up with different types of single button interactions (e.g. long button press, short button press, double press, etc.) to cover all operations or interactions.

In an example, gas detectors often require regular calibration (i.e. apply a known gas, read the sensor output, and adjust gas readings as needed) and bumping (i.e. apply a known gas to make sure all user alerts are still working as intended). Usually these actions are completed within a docking station or manually. When done manually, the problem described above may arise, where if there is only one button, it may be difficult to control the device to enter calibration or bump mode.

Applicants have proposed a process using near field communication (NFC) between the gas detectors and one or more NFC tag. The tube that supplies the gas sample to the detector that is used for calibration (cal) and bumping (bump) may be redesigned to incorporate a passive NFC tag near the end of the tubeoperable to attach to the detector device. The NFC tag will contain information such as gas type, concentration, and the action required (bump or cal). To interact with the NFC tag, an NFC reader may be incorporated into the gas detector. When the tube is in place it will be in close enough proximity of the reader that the device will automatically read the information off the tube's NFC tag and put the device in to the appropriate mode. The proposed solution requires no interaction between the user and the device other than attaching the tube, reducing the potential for error, and reducing the time required for the bump/cal process.

Referring now to FIG. 1A, a system 100 may comprise a detector device 102, such as a gas detector, one or more gas delivery tubes 104, and one or more NFC tags 105 attached to the gas delivery tubes 104. In some embodiments, the gas delivery tubes 104 may be part of a gas testing system. The detector 102 may comprise an attachment point 103 operable to connect to the gas delivery tube(s) 104 and an NFC reader 106. The NFC reader 106 may be operable to receive input from the NFC tag(s) 105. In some embodiments, the gas detector device may comprise a memory 112 and a processor 114. Additionally, the gas detector device may comprise an application stored in the memory 112, that when executed by the processor 114 receives instructions from the NFC tag 105 via the NFC reader 106, and executes an action based on the instructions from the NFC tag 105.

Figure 1B:
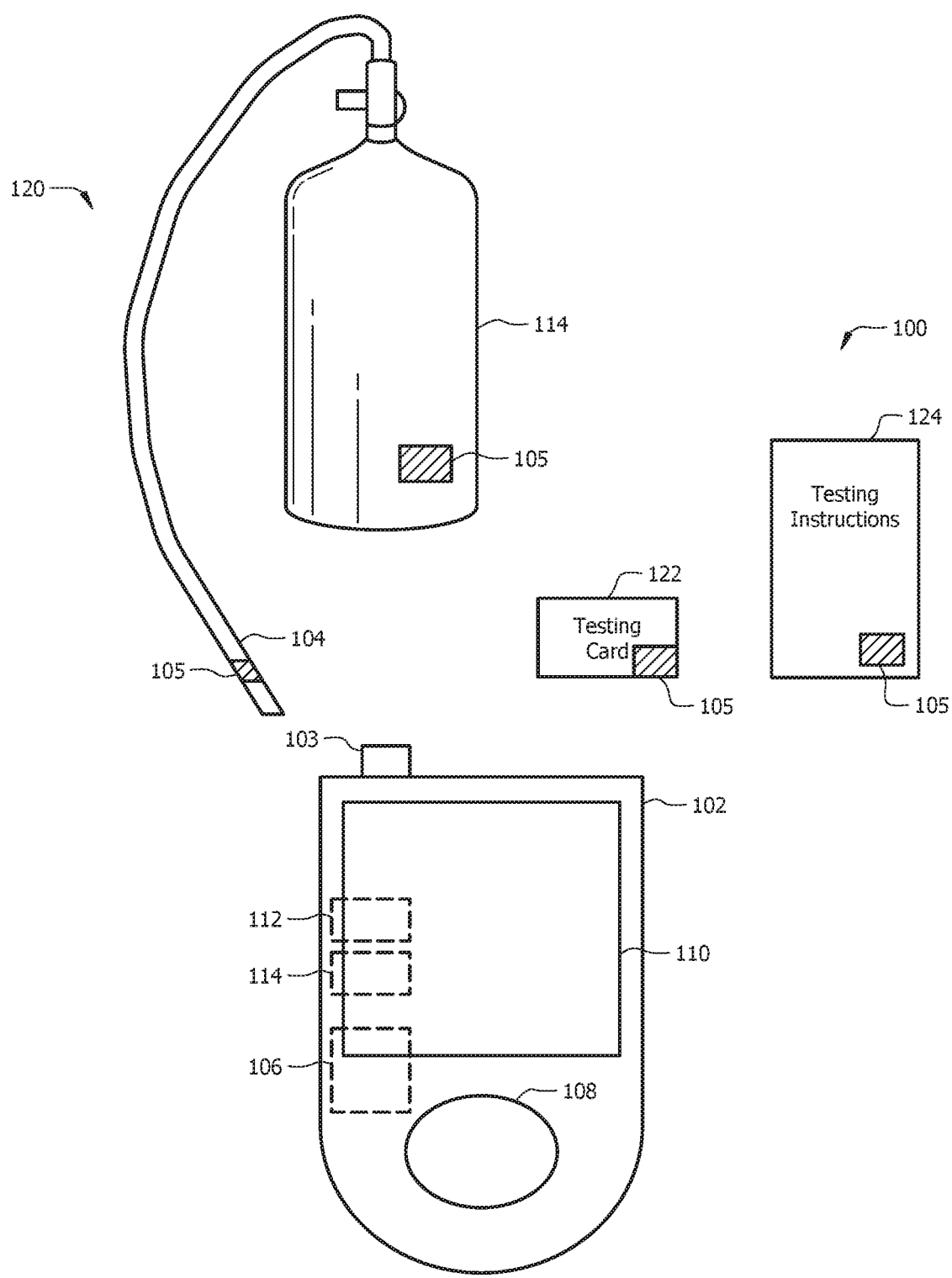
FIG. 1B illustrates a gas detector and gas testing system according to an embodiment of the disclosure.

Referring to FIG. 1B, the system 100 may comprise a full gas testing system 120. In some embodiments, the NFC tag(s) 105 may be attached to the gas delivery tube 104 (as described above). Alternatively, the NFC tag(s) 105 may be attached to a gas tank 114 (which may deliver gas to the detector via a gas delivery tube 104). In alternative embodiments, the NFC tag(s) 105 may be attached to any part of the gas testing system 120, including the gas tank, the gas delivery tubes, and the area around the gas tank, for example. In some embodiments, the gas testing system 120 may comprise a testing card 122 comprising the NFC tag 105, wherein a user may swipe the card 122 near the gas detector device 102 to communicate the information. In some embodiments, the gas testing system 120 may comprise a poster 124 comprising the NFC tag 105, Wherein a user may swipe the gas detector device 102 near the poster 124 to communicate the information.

In FIGS. 1A-1B, the detector 102 may comprise a single button 108 for interaction with a user. This may simplify the interactions required by a user, which may be hindered by a user wearing protective gear, such as gloves. In some embodiments, the detector 102 may also comprise a user interface 110, which may include a screen, a microphone, a speaker, etc., for interaction between the user and the detector 102.

Figure 2B:
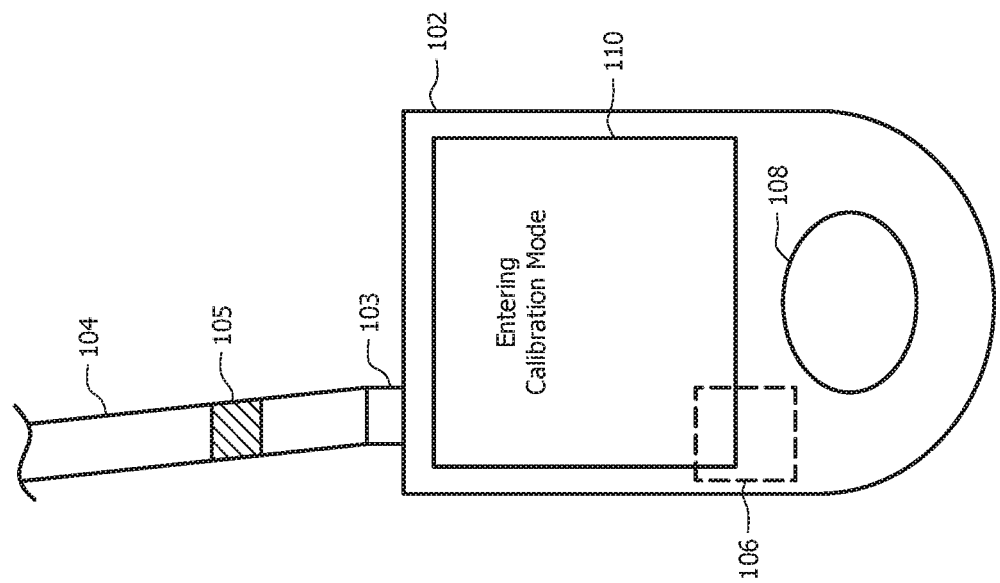
FIGS. 2A-2B illustrate the operation of a gas detector and gas testing system communicating via NFC.
Figure 2A:
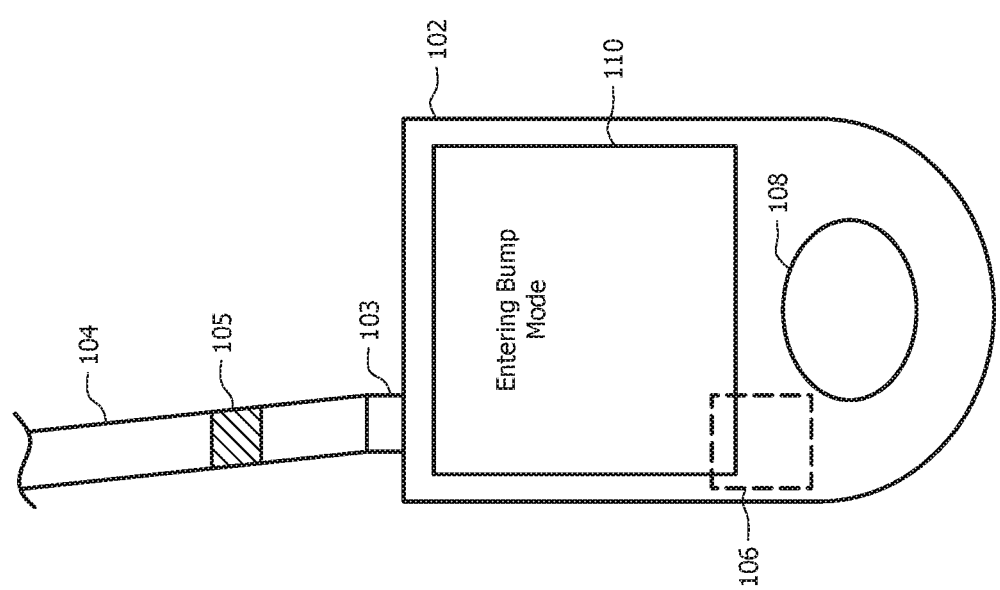

Referring to FIGS. 2A-2B, the gas delivery tube 104 may attach to the detector 102, and the NFC reader 106 of the detector 102 may interact with one of the NFC tags 105 to execute different actions, operations, or processes on the detector 102, as described above. In FIG. 2A the NFC tag 105 may initiate a bump process, by prompting the device to enter bump mode. In FIG. 2B the NFC tag 105 may initiate a calibration, by prompting the device to enter calibration mode. In other embodiments, additional NFC tags 105 may be used to initiate different actions on the detector 102.

Embodiments of the disclosure may comprise a gas detector device comprising a processor; a memory; a near field communication (NFC) reader; an attachment point operable to attach to one or more gas delivery tubes, wherein the gas delivery tube comprises an NFC tag operable to interact with the NFC reader of the gas detector to give instructions to the detector; and an application stored in the memory, that when executed by the processor receives instructions from the NFC tag via the NFC reader, and executes an action based on the instructions from the NFC tag.

In some embodiments, the NFC tag may instruct the detector to enter bumping mode. In some embodiments, the NFC tag may instruct the detector to enter calibration mode. In some embodiments, the gas delivery tube delivers gas to the gas detector to complete the action executed by the detector. In some embodiments, the gas detector is operable to attach to a plurality of gas delivery tubs and complete a plurality of actions. In some embodiments, the gas detector comprises a single button for interaction between a user and the detector. In some embodiments, the gas detector comprises a user interface for interaction between a user and the detector.

Embodiments of the disclosure may comprise a gas detector device comprising a processor; a memory; a near field communication (NFC) reader; an attachment point operable to attach to a gas testing system, wherein the gas testing system comprises an NFC tag operable to interact with the NFC reader of the gas detector to give instructions to the detector; and an application stored in the memory, that when executed by the processor receives instructions from the NFC tag via the NFC reader, and executes an action based on the instructions from the NFC tag.

In some embodiments, the gas detector device may comprise a gas sensor. In some embodiments, the gas sensor may receive the gas delivered by the gas delivery tube. In some embodiments, the gas testing system comprises a gas delivery tube operable to deliver gas to the gas detector to complete the action executed by the detector. In some embodiments, the gas testing system comprises one or more gas delivery tubes and one or more gas tank.

Additional embodiments of the disclosure may comprise a method for completing an action on a gas detector device comprising: connecting, by the gas detector device, to a gas delivery tube of a gas testing system, wherein the gas delivery tube comprises a near field communication (NFC) tag; receiving, via an NFC reader of the gas detector device, instructions from the NFC tag for completing an action on the gas detector device; executing, by the gas detector device, the instructions received from the NFC tag via the NFC reader to complete the action on the gas detector device; and receiving sample gas output from the gas delivery tube to complete the action on the gas detector device. In some embodiments, the sample may be received by a sensor of the gas detector device.

In some embodiments, the method may further comprise connecting, by the gas detector device, to a second gas delivery tube of the gas testing system, wherein the gas testing system comprises a second NFC tag; receiving, via the NFC reader of the gas detector device, instructions from the second NFC tag for completing a second action on the gas detector device; executing, by the gas detector device, the instructions received from the second NFC tag via the NFC reader to complete the second action on the gas detector device; and receiving sample gas output from the second gas delivery tube to complete the second action on the gas detector device. In some embodiments, the action comprises entering into bumping mode. In some embodiments, the method may further comprise completing a bump process by the gas detector. In some embodiments, the action comprises entering into calibration mode. In some embodiments, the method may further comprise completing a calibration process by the gas detector. In some embodiments, the NFC tag may be located on the gas delivery tube. In some embodiments, the gas detector comprises a single button for interaction between a user and the detector.

Other embodiments of the disclosure may include a system for providing automatic interaction with gas detectors comprising: a gas testing system comprising one or more gas tanks containing sample gas for testing a gas detector device; one or more gas delivery tubes operable to attach to a gas detector device; and an NFC tag attached to each of the one or more gas delivery tubes. The system may also comprise a gas detector device comprising: a processor; a memory; a near field communication (NFC) reader, wherein the NFC tag of the gas delivery tubes is operable to interact with the NFC reader of the gas detector device to communicate instructions to the gas detector device; an attachment point operable to attach to the one or more gas delivery tubes; and an application stored in the memory, that when executed by the processor receives instructions from the NFC tag via the NFC reader, and executes an action based on the instructions from the NFC tag.

In some embodiments, the NFC tag instructs the detector to enter bumping mode. In some embodiments, the NFC tag instructs the detector to enter calibration mode. In some embodiments, the gas delivery tube delivers gas to the gas detector to complete the action executed by the detector. In some embodiments, the gas detector is operable to attach to a plurality of gas delivery tubs and complete a plurality of actions. In some embodiments, the gas detector comprises a single button for interaction between a user and the detector, and a user interface for interaction between a user and the detector.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises", "includes", and "having" should be understood to provide support for narrower terms such as "consisting of", "consisting essentially of", and "comprised substantially of". Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detection device comprising:
    a processor;
    a memory;
    a near field communication reader configured to wirelessly interact with at least one near field communication tag that is configured to be removably coupled to a gas testing system, the near field communication reader configured to receive, from the near field communication tag, information comprising at least one instruction that is representative of an action to be carried out by the gas detection device; and
    an application stored in the memory that, when executed by the processor, receives the information comprising the at least one instruction for the action to be carried out by the gas detection device from the near field communication tag via the near field communication reader, and executes the action based on the information received from the near field communication tag.

2. The device of claim 1, wherein the near field communication reader is configured to receive information from the near field communication tag comprising an instruction for the gas detection device to enter a bumping mode.

3. The device of claim 1, wherein the near field communication reader is configured to receive information from the near field communication tag comprising an instruction for the gas detection device to enter a calibration mode.

4. The device of claim 1, further comprising:
    an attachment point configured to be removably coupled to the gas testing system,
    wherein the attachment point is configured to receive one or more sample gases from the gas testing system before or during completion of the action by the gas detection device.

5. The device of claim 4, wherein the gas detection device is configured to attach to a plurality of gas delivery tubes and complete a plurality of actions.

6. The device of claim 1, wherein the gas detection device comprises a single button for interaction between a user and the gas detection device.

7. The device of claim 1, wherein the gas testing system comprises one or more gas delivery tubes and a gas tank.

8. A method comprising:
connecting, by an attachment point of a gas detection device, to a gas delivery tube of a gas testing system, wherein the gas testing system is configured to supply a gas to the attachment point of the gas detection device via the gas delivery tube;
wirelessly receiving, from a near field communication tag of the gas testing system, via a near field communication reader of the gas detection device, information comprising at least one instruction for an action to be carried out by the gas detection device;
executing, by the gas detection device, the at least one instruction received from the near field communication tag to complete the action; and
receiving a volume of a sample gas, output from the gas delivery tube, to a sensor of the gas detection device such that the gas detection device is able to complete the action.

9. The method of claim 8, further comprising:
connecting, by the gas detection device, to a second gas delivery tube of the gas testing system, wherein the gas testing system comprises a second near field communication tag;
wirelessly receiving, by the near field communication reader of the gas detection device, from the second near field communication tag, second information comprising at least one second instructions for a second action to be carried out by the gas detection device;
executing, by the gas detection device, the at least one second instructions received from the second near field communication tag to complete the second action; and
receiving a second volume of the sample gas or a volume of a second sample gas from the second gas delivery tube to a sensor of the gas detection device to complete the second action.

10. The method of claim 8, wherein the action comprises causing the gas detection device to enter into a bumping mode.

11. The method of claim 10, further comprising:
completing, using the gas detection device, a bump process.

12. The method of claim 8, wherein the action comprises causing the gas detection device to enter into a calibration mode.

13. The method of claim 12, further comprising:
completing, using the gas detection device, a calibration process.

14. The method of claim 8, wherein the near field communication tag is located on the gas delivery tube.

15. The method of claim 8, wherein the gas detection device comprises a single button for interaction between a user and the gas detection device.

16. A system comprising:
a gas testing system comprising:
one or more gas tanks containing a volume of a sample gas;
one or more gas delivery tubes coupled to a respective gas tank of the one or more gas tanks and configured to communicate at least a portion of the sample gas therethrough; and
a near field communication tag, wherein the near field communication tag is configured to store information related to at least one instruction for an action to be carried out; and
a gas detection device comprising:
a processor;
a memory;
a near field communication reader configured to wirelessly interact with the near field communication tag of the gas testing system, the near field communication reader configured to receive, from the near field communication tag, the information comprising at least one instruction for the action to be carried out by the gas detection device;
an attachment point configured to be removably coupled to the one or more gas delivery tubes in order to receive a supply of the sample gas from the gas testing system; and
an application stored in the memory that, when executed by the processor, receives the information comprising the at least one instruction for the action to be carried out by the gas detection device from the near field communication tag via the near field communication reader, and executes the action based on the information received from the near field communication tag.

17. The system of claim 16, wherein the near field communication tag is configured to store information comprising an instruction for the gas detection device to enter a bumping mode.

18. The system of claim 16, wherein the near field communication tag is configured to store information comprising an instruction for the gas detection device to enter a calibration mode.

19. The system of claim 16, wherein the gas delivery tube is configured to deliver gas to the attachment point of the gas detection device such that the gas detection device is able to complete the action.

20. The system of claim 16, wherein the gas detection device comprises a single button for interaction between a user and the gas detection device.

* * * * *